United States Patent [19]
Richards et al.

[11] Patent Number: 5,159,943
[45] Date of Patent: Nov. 3, 1992

[54] UNIFIED DENTAL FLOSS AND BRIDGE THREADER

[76] Inventors: Linda K. Richards; Norvel D. Richards, both of 8094 Olney St., SE., Salem, Oreg. 97301

[21] Appl. No.: 795,391

[22] Filed: Nov. 21, 1991

[51] Int. Cl.⁵ .............................................. A61C 15/00
[52] U.S. Cl. .................................... 132/321; 132/323
[58] Field of Search ....................... 132/321, 323, 324

[56] References Cited

U.S. PATENT DOCUMENTS

| | | | |
|---|---|---|---|
| 3,930,059 | 12/1975 | Wells | 132/321 |
| 4,008,727 | 2/1977 | Thornton | 132/321 |
| 4,034,770 | 7/1977 | Trecker | 132/321 |
| 4,142,538 | 3/1979 | Thornton | 132/321 |
| 4,941,487 | 7/1990 | Van Beneden | 132/323 |
| 4,974,615 | 12/1990 | Doundoulakis | 132/321 |
| 4,982,752 | 1/1991 | Rodriguez | 132/324 |
| 4,986,288 | 1/1991 | Kent et al. | 132/321 |

*Primary Examiner*—John J. Wilson
*Attorney, Agent, or Firm*—S. Michael Bender

[57] ABSTRACT

A dental floss dispenser is designed to retain a roll of dental floss which may be dispensed and cut through an opening. The floss is provided in preselected lengths interconnected by shorter lengths of thread. Once dispensed and cut in a medial portion of the thread, the threaded ends of a length of floss may be held to use the floss which prevents any wastage of flossing material. In modified embodiments, the lengths of thread may be provided with small knots to indicate where to cut the thread and to provide a better grip during a use of the floss. Further, granules of fluoride may be attached to a floss strip to act both as an abrasive and as a means of applying fluoride between teeth as the granules dissolve.

1 Claim, 4 Drawing Sheets

UNIFIED DENTAL FLOSS AND BRIDGE THREADER

BACKGROUND OF THE INVENTION

1. Field of the Invention

The present invention relates to dental floss and more particularly pertains to a new and improved form of dental floss which may be dispensed from a container and which provides means for preventing wastage of flossing material.

2. Description of the Prior Art

The use of dental floss and associated dispensers is well known in the prior art. Typical examples of such prior art dental floss dispensers include U.S. Pat. No. 4,901,742, which issued to M. Olson on Feb. 20, 1990, and U.S. Pat. No. 4,920,993, which issued to K. Mackie on May 1, 1990. Both of these prior art patents are illustrative of the current state of the art with respect to dental floss and its associated dispenser arrangements. However, neither of these devices are particularly effective in measuring prescribed lengths of dental floss, nor is the dental floss employed therewith designed to facilitate a lack of wastage or improved cleaning characteristics. As such, there appears to be a continuing need for new types of dental floss and its associated dispenser arrangements wherein such floss might be utilized in an improved manner for cleaning a user's teeth as well as to prevent wastage of flossing material. In this respect, the present invention substantially fulfills this need.

SUMMARY OF THE INVENTION

In view of the foregoing disadvantages inherent in the known types of dental floss assemblies now present in the prior art, the present invention provides an improved dental floss construction wherein the floss is designed to have improved cleaning characteristics as well as usage techniques to prevent wastage of flossing material, while an associated dispenser is designed to accommodate these improvements. As such, the general purpose of the present invention which will be described subsequently in greater detail, is to provide a new and improved dental floss assembly which has all the advantages of the prior art dental floss assemblies and none of the disadvantages.

To attain this, the present invention essentially comprises a dental floss dispenser is designed to retain a roll of dental floss which may be dispensed and cut through an opening. The floss is provided in preselected lengths interconnected by shorter lengths of thread. Once dispensed and cut in a medial portion of the thread, the threaded ends of a length of floss may be held to use the floss which prevents any wastage of flossing material. In modified embodiments, the lengths of thread may be provided with small knots to indicate where to cut the thread and to provide a better grip during a use of the floss. Further, granules of fluoride may be attached to a floss strip to act both as an abrasive and as a means of applying fluoride between teeth as the granules dissolve.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved dental floss assembly which has all the advantages of the prior art dental floss assemblies and none of the disadvantages.

It is another object of the present invention to provide a new and improved dental floss assembly which may be easily and efficiently manufactured and marketed.

It is a further object of the present invention to provide a new and improved dental floss assembly which is of a durable and reliable construction.

An even further object of the present invention is to provide a new and improved dental floss assembly which is susceptible of a low cost of manufacture with regard to both materials and labor, and which accordingly is then susceptible of low prices of sale to the consuming public, thereby making such dental floss assemblies economically available to the buying public.

Still yet another object of the present invention is to provide a new and improved dental floss assembly which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
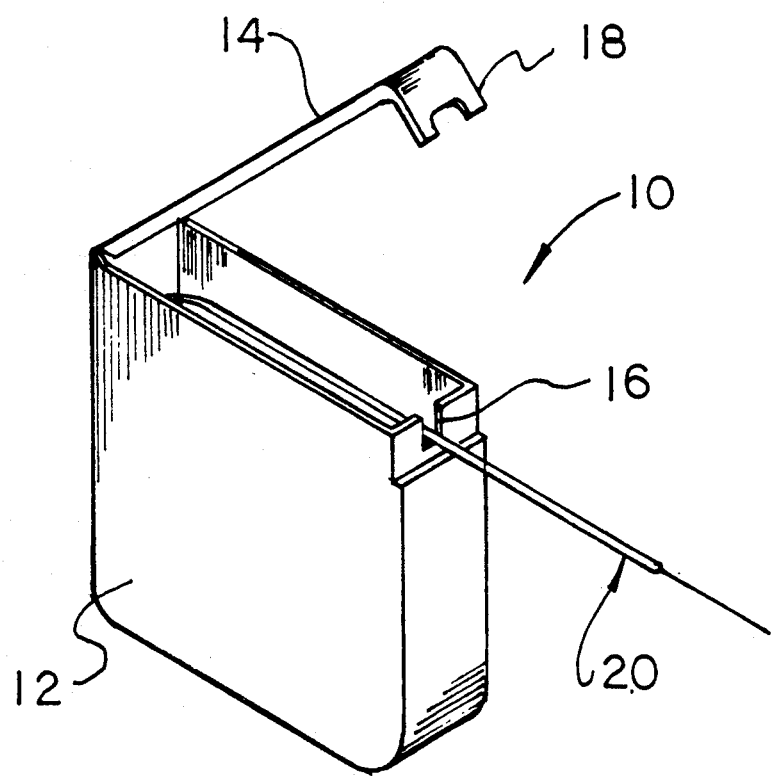
FIG. 1 is a perspective view of the floss assembly comprising the present invention.
Figure 2:
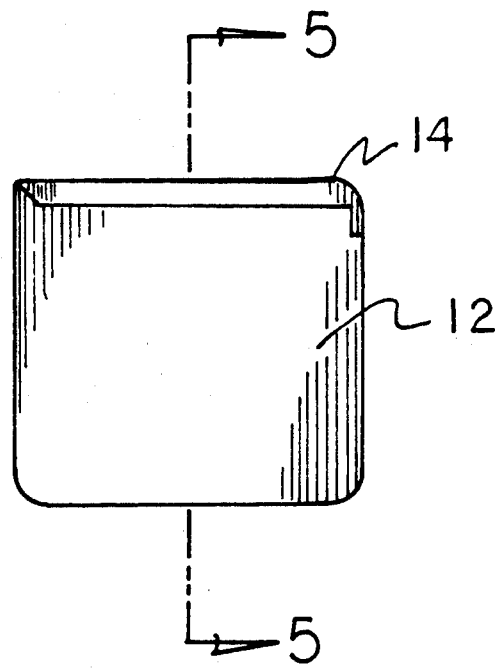
FIG. 2 is a side elevation view of the invention.
Figure 3:
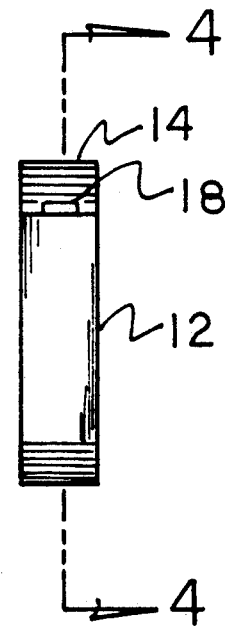
FIG. 3 is an end elevation view of the invention.

With reference now to the drawings, and in particular to FIGS. 1-5 thereof, a new and improved dental floss assembly embodying the principles and concepts of the present invention and generally designated by the reference numeral 10 will be described.

Figure 4:
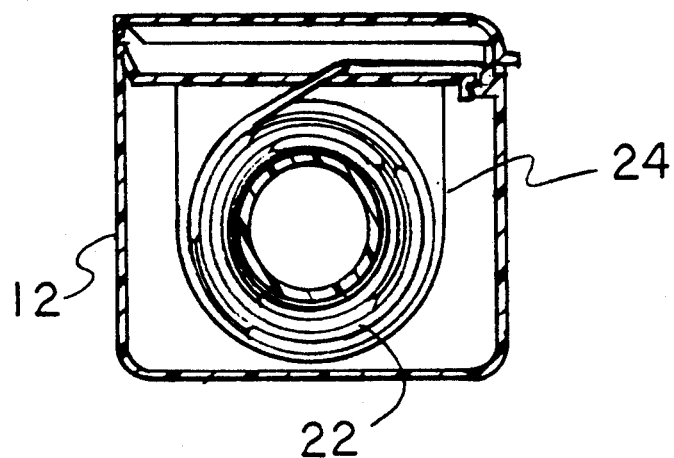
FIG. 4 is a cross-sectional view of the invention as viewed along the line 4—4 in FIG. 3.
Figure 5:
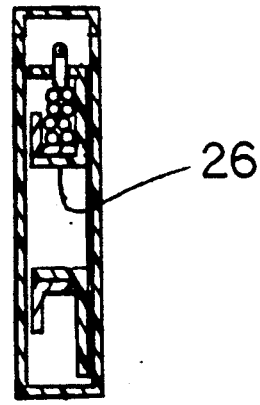
FIG. 5 is a cross-sectional view of the invention as viewed along the line 5—5 in FIG. 2.

As shown, the dental floss assembly 10 includes a housing 12 having a pivotally movable lid 14 attached thereto. A guide slot 16 is formed in a top portion of the housing 12 and a further slot 18 formed in the lid 14 cooperates with the slot 16 to form a dispensing orifice for a length of dental floss 20. In this regard, a roll of dental floss 22 is positionable within a cavity 24 formed in the housing 12 as best shown in FIG. 4, and the floss 22 is mounted upon a rotatable spool 26 retained within the cavity.

Figure 6:
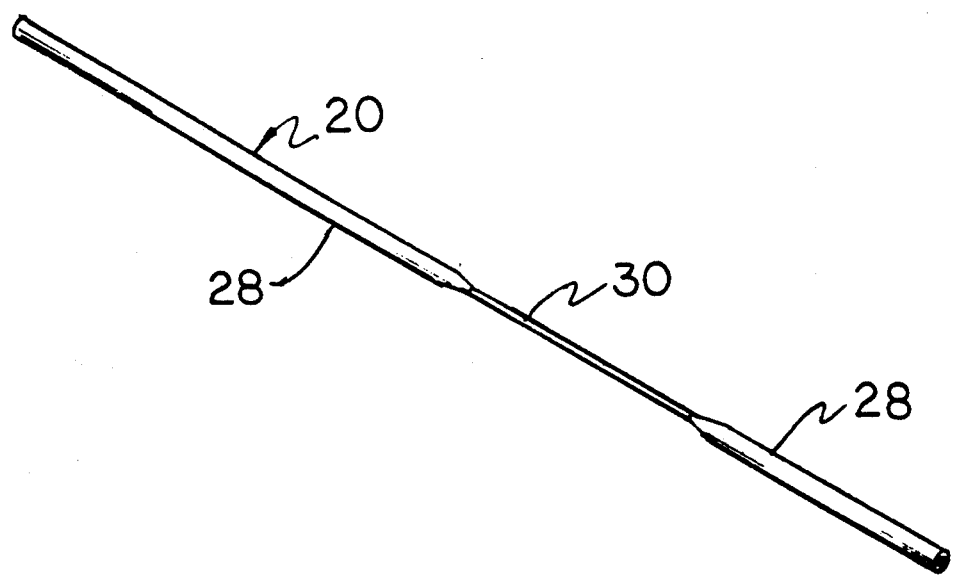
FIG. 6 is a perspective view of a length of floss forming a part of the present invention.

A particular feature of the present invention is the novel construction of the floss 20 wherein it is designed to prevent wastage. As best illustrated in FIG. 6, the floss 20 consists of a plurality of ten inch lengths of floss 28, each of which is interconnected to the next in line by a one and one-half inch length of thin thread 30. Any manufacturing process could be utilized to interconnect the thread 30 with a plurality of lengths of floss 28 and in this regard, it is even conceivable that the thread 30 be of a continuous length with the floss 28 being fixedly secured thereto by some known method of attachment.

With respect to the usage of the floss 20, it can be appreciated that ten inch lengths of floss 28 can be dispensed through the combined orifice structure 16, 18, and when the thread 30 becomes visible, a cutter mounted within the orifice structure can be used to snip through the thread. The thread 30 at each end of a length of floss 28 can then be gripped by a user so that a complete usage of the floss can be obtained and no wastage occurs along a section which would normally be gripped by a user's fingers.

Figure 7:
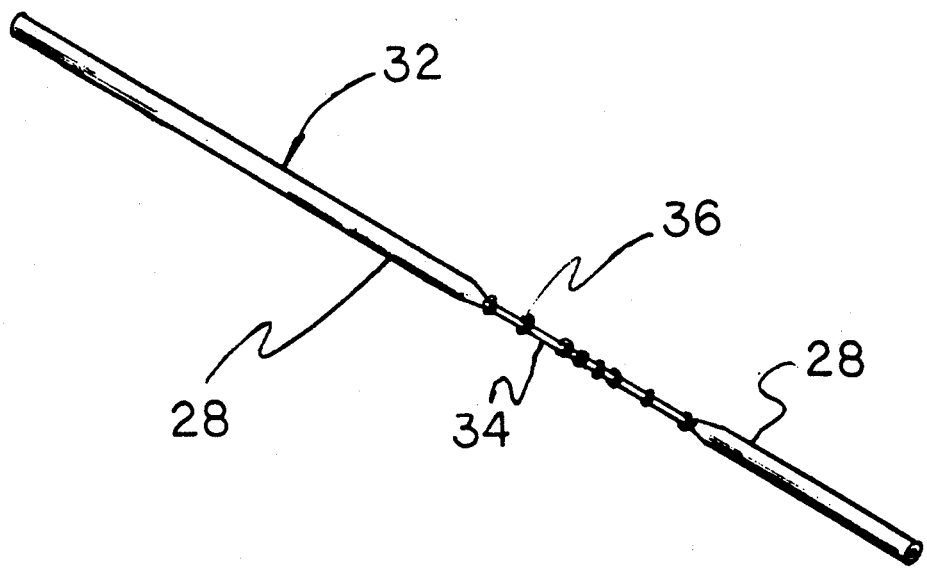
FIG. 7 is a perspective view of a modified length of floss.

FIG. 7 of the drawings illustrates a modified embodiment of the floss which is generally designated by the reference numeral 32. Again, lengths 28 of floss are joined together by a length of thread which is now designated by the reference numeral 34. In this regard, the length of thread 34 is provided with a plurality of small knots 36 which operate to indicate where a user should cut through the thread as it is being dispensed from the housing 12 and further, the knots improve the grip of a user who is holding onto the thread during a usage of the floss.

Figure 8:
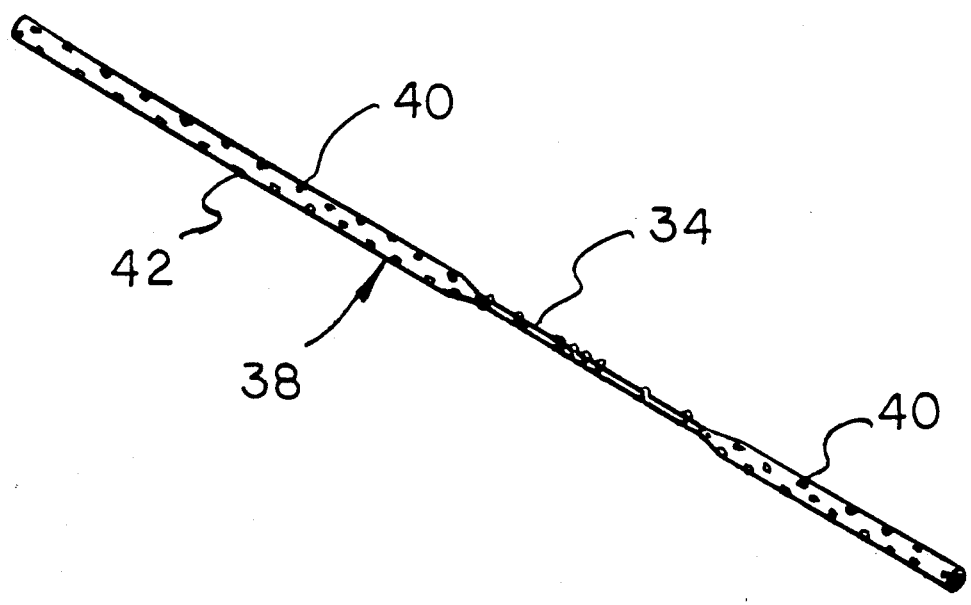
FIG. 8 is a perspective view of a further embodiment of floss utilizable with the present invention.
Figure 9:
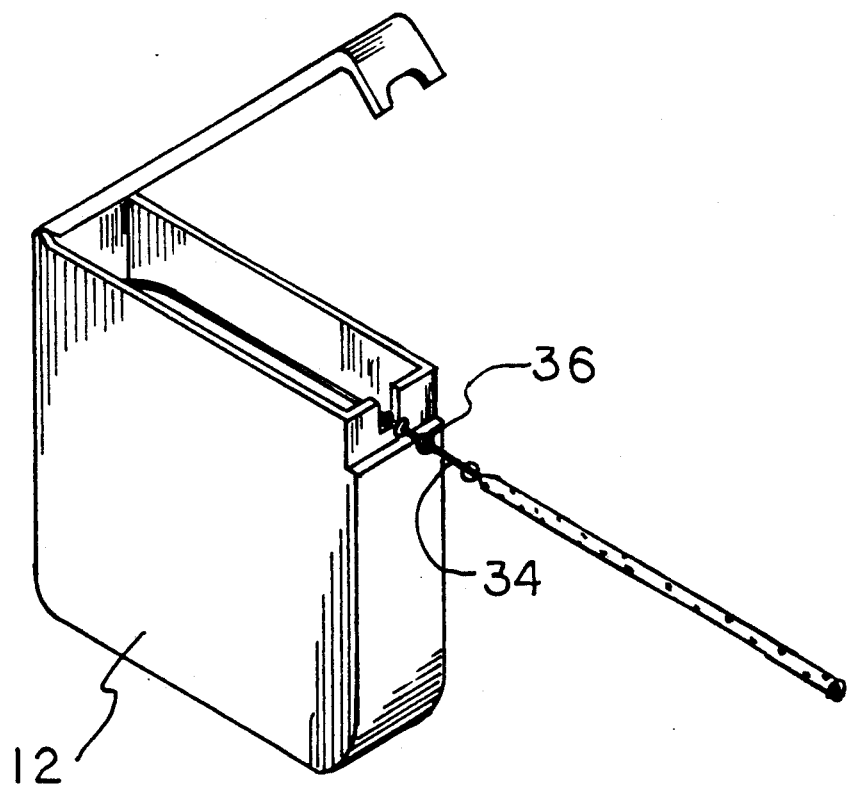
FIG. 9 is a perspective view of the third embodiment of floss operably positioned within a dispenser.

FIGS. 8 and 9 of the drawings illustrate a further modified embodiment of floss which is generally designated by the reference numeral 38. This further embodiment utilizes a knotted thread assembly 34 as was utilized with the embodiment 32; however, granules of fluoride 40 are interspersed along and attached to ten inch lengths of floss 42. These granules of fluoride initially act as an abrasive as the floss 42 is being used and, as use continues, they dissolve so as to effectively provide a mild fluoride coating to the surfaces between a user's teeth. This embodiment of floss 38 may also be dispensed from the same type of dispenser 12 as clearly indicated in FIG. 9, with this figure also making it evident how to utilize the knots 36 as a means of determining where to cut through a section of thread 34.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved dental floss assembly comprising:

a plurality of preselected lengths of dental floss;

connection means interfixed between each of said plurality of preselected lengths of dental floss, said connection means comprising short lengths of thread fixedly secured to free ends of said plurality of preselected lengths of dental floss;

dispenser means for said dental floss, said dispenser means having a pivotally attached lid;

a spool forming a part of said dispenser means, said spool retaining and facilitating a dispensing of said dental floss;

an orifice provided in said lid for facilitating a dispensing of said dental floss, said orifice also having a cutter associated therewith for facilitating a severance of said dental floss when desired;

a plurality of granules of fluoride interspersed along each of said plurality of preselected lengths of dental floss, said granules of fluoride acting as an abrasive and being dissolvable to allow a coating of fluoride to be obtained between a user's teeth; and a plurality of small knots on said thread, thereby to facilitate both a gripping of said thread and a determination of where to sever said thread in order to obtain a single one of said plurality of preselected lengths of dental floss, said plurality of small knots including closely spaced-apart knots and further apart knots, said closely spaced-apart knots being medially positioned on said thread and being used to determine where to sever said thread with said cutter, and used further apart knots being positioned proximate said free ends of said dental floss and being utilizable to facilitate said gripping of said thread during an operational use of said dental floss by said user.

* * * * *